United States Patent [19]
Karpisek

[11] Patent Number: 4,869,721
[45] Date of Patent: Sep. 26, 1989

[54] FLOW REGULATOR FOR LIQUIDS

[76] Inventor: Ladislav S. Karpisek, 86 Woodfield Blvd., Caringbah, New South Wales, Australia, 2229

[21] Appl. No.: 137,538

[22] PCT Filed: Feb. 6, 1987

[86] PCT No.: PCT/AU87/00034
§ 371 Date: Sep. 29, 1987
§ 102(e) Date: Sep. 29, 1987

[87] PCT Pub. No.: WO87/04932
PCT Pub. Date: Aug. 27, 1987

[30] Foreign Application Priority Data
Feb. 12, 1986 [AU] Australia .............................. PH 4551

[51] Int. Cl.$^4$ .............................................. A61M 5/14
[52] U.S. Cl. ......................................... 604/250; 251/6
[58] Field of Search ....................... 604/34, 250; 251/4, 251/6

[56] References Cited
U.S. PATENT DOCUMENTS

| | | |
|---|---|---|
| 2,595,511 | 5/1952 | Butler ..................................... 251/6 |
| 3,893,468 | 7/1975 | McPhee .................................. 251/6 |
| 3,918,675 | 11/1975 | Forberg .................................. 251/6 |
| 4,238,108 | 12/1980 | Muetterties ............................. 251/6 |
| 4,270,725 | 6/1981 | Scott et al. ............................. 251/6 |
| 4,662,599 | 5/1987 | Attermeier .............................. 251/6 |

Primary Examiner—Stephen C. Pellegrino
Assistant Examiner—Ralph Lewis
Attorney, Agent, or Firm—Anthony A. O'Brien

[57] ABSTRACT

A flow regulator for liquids passing through a resiliently deformable tube (18), the regulator comprising a body including a channel (8) to receive the tube (18), a channel floor (10) less than the length of the body, two axle tracks (12) in the inner faces of the channel walls (9) extending over the channel floor (10), a wheel (13) supported by stub axles (14) in the tracks (12) and a groove (15) of varying cross-sectional size in the channel floor (10) into which the tube (18) is forced as the wheel (13) passes over the groove (15).

4 Claims, 3 Drawing Sheets

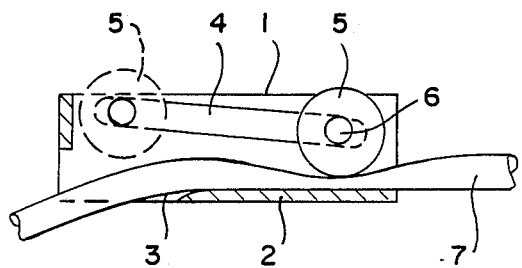
FIG. 1 PRIOR ART
FIG. 2 PRIOR ART
FIG. 3 PRIOR ART
FIG. 4 PRIOR ART
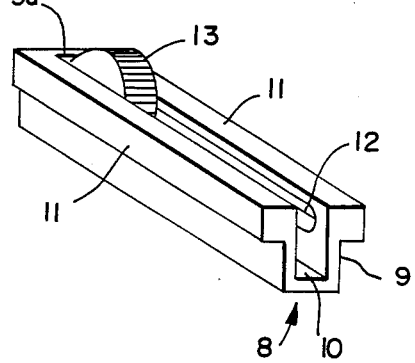
FIG. 5
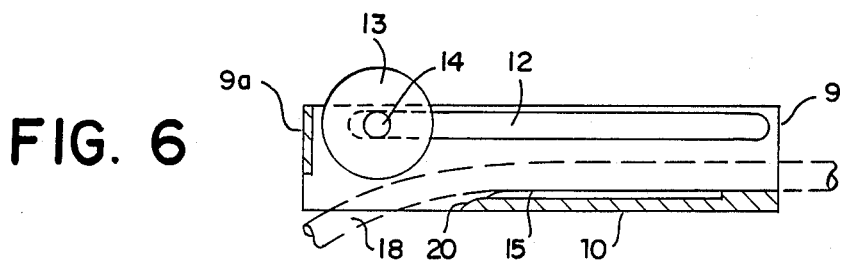
FIG. 6
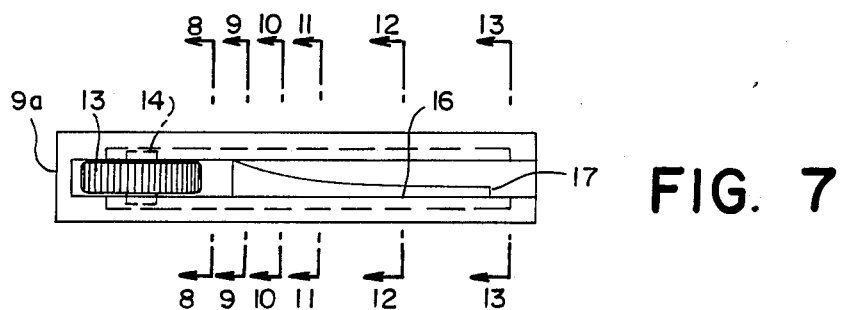
FIG. 7

FIG. 8    FIG. 9    FIG. 10
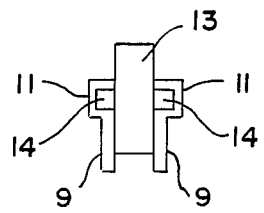 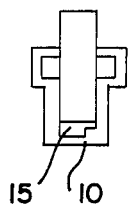 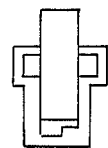
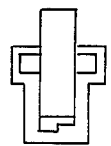 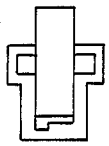 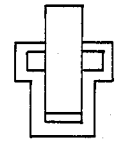
FIG. 11   FIG. 12   FIG. 13
FIG. 14   FIG. 15   FIG. 16
  
FIG. 17   FIG. 18   FIG. 19
  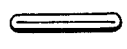

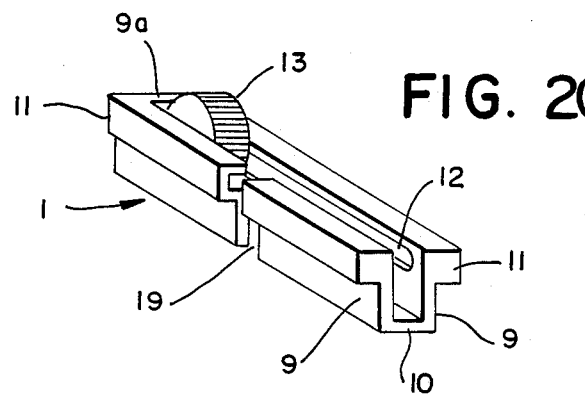
FIG. 20
FIG. 21
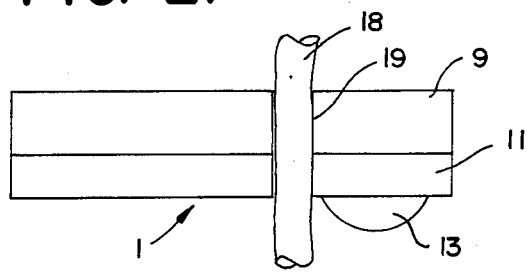
FIG. 22
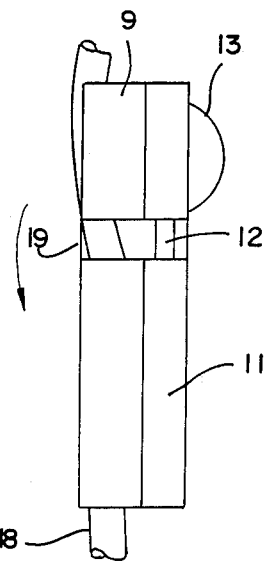
FIG. 23
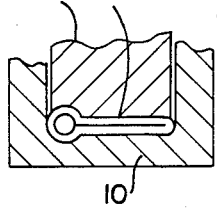
FIG. 24
FIG. 25
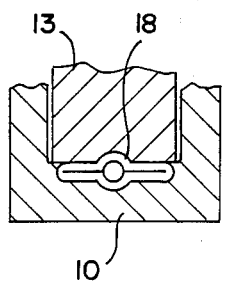
FIG. 26

FLOW REGULATOR FOR LIQUIDS

This invention provides means to control the flow of liquids and has particular relevance to controlling liquid flows that have to be regulated accurately and are small in volume. Examples of uses for the proposed apparatus is in the regulation of the flow of liquids through devices whereby blood or saline solution or like liquids are introduced intravenously to patients.

In one presently used apparatus for the above purpose liquid passes through a fixed size discharge orifice from a first chamber member into an elongated orifice of tapered shape in a second member, the maximum cross-section of the tapered orifice being smaller than the fixed size orifice. The tapered orifice discharges into a tube to deliver the liquid to its destination. The first member and the second member are movable one relative to the other to bring the fixed size orifice in the first member over different portions of the second orifice, the size of the portion of the second orifice exposed to the fixed size orifice can thus be varied and this determines the rate of flow of the liquid.

This form of apparatus has two major disadvantages. Firstly the liquid passes through the device and therefore sterilization of the parts of the device is required. Secondly, there are locations in the device where the liquid flows very slowly or may even cease to flow allowing blood co-agulation can occur.

In another form of device which operates much the same as the apparatus proposed by this invention, there is a plastic tube through which the liquid flows from a supply to a destination. The tube passes through a clamp means which by squeezing the tube transforms the circular bore of the tube into an elongated parallel sided slit with the width of the slit being the principal determining factor for controlling the flow rate of liquid through the tube. This has the disadvantage that as the slit becomes narrower the flow of liquid equates to a film with an increase in frictional drag which tends to inhibit flow. When the film is very thin blood co-agulation can readily occur. The use of the device usually involves constant supervision to ensure the required flow rate is maintained.

Another problem with known apparatus is the difficulty in accurately setting the flow rate where small flow rates are required and the apparatus acts as a restrictor to provide a thin film flow. Where the apparatus in being handled heat from the hand of an operator can cause expansion of the apparatus and when the apparatus returns to ambient temperature the flow rate will be different from that originally set by the operator. In addition, where thin film flows are caused by the apparatus and assuming no coagulation of the liquid flowing, there is a significant variation in the flow rate as the volume in the reservoir drops. In other words the flow rate is very sensitive to the hydraulic head acting on the liquid. This is negated to a large extent where thin film flows are avoided.

Despite the disadvantages outlined above which occur with the "squeeze" method for controlling the flow of liquid through a delivery tube there are compensating aspects. The system is simple, there is no sterilization problems as with the first known arrangement described above and the equipment is inexpensive. The present invention provides apparatus to overcome most of the disadvantages of the squeeze method by providing a minimum surface area of the bore of the tube for all cross-sections the tube adopts during the sqeezing process right down to the throttle condition where the flow is completely stopped. This is achieved by the progressive reduction of the cross-section of the bore of the tube while maintaining the cross-sectional shape of the bore of the tube substantially circular.

Broadly, the invention can be said to comprise a flow regulator for liquids passing through a resiliently deformable tube, the regulator comprises an elongated body part including a channel having a floor and two parallel sides which extend in the length direction of the channel beyond one end of the channel floor, a groove in the floor of the channel which decreases in width along its length and has the greatest width adjacent said one end of the channel floor, a longitudinal track in each channel wall, said tracks are parallel to each other and are the same height above the channel floor and extend beyond said one end of the channel floor, a wheel with a central stub axle projecting from each side of the wheel, the diameter of the wheel being such that with the stub axles captive in the grooves and the wheel positioned over the channel floor the distance between the channel floor and the closest part of the periphery of the wheel will never be greater than twice the thickness of the wall of a deformable tube to be mounted in the channel of the regulator.

Several preferred embodiments of the invention will now be described with reference to the accompanying drawings in which:

FIG. 1 is a sectional elevation of a known form of flow regulator,

FIG. 2 is an end view of a tube when partially flattened in the FIG. 1 apparatus, FIG. 3 is a view similar to FIG. 2 showing the tube further flattened, FIG. 4 is a view similar to fig.2 showing the tube fully flattened, FIG. 5 is a perspective view of one embodiment of the flow regulator of this invention, FIG. 6 is a sectional elevation of the regulator of FIG. 5, FIG. 7 is a plan view of the FIG. 5 regulator, FIG. 8 is a sectional end view on the section line 8—8 of FIG. 7, FIG. 9 is a sectional end view on the section line 9—9 of FIG. 7, FIG. 10 is a sectional end view on the section line 10—10 of FIG. 7, FIG. 11 is a sectional end view on the section line 11—11 of FIG. 7, FIG. 12 is a sectional end view on the section line 12—12 of FIG. 7, FIG. 13 is a sectional end view on the section line 13—13 of FIG. 7, FIG. 14 is an end view of a tube prior to flattening in the regulator of the invention, FIG. 15 is an end view of a tube when flattened in the regulator of the invention at the section line 9—9 of FIG. 7, FIG. 16 is an end view of a tube when flattened in the regulator of the invention at the section line 10—10 of FIG. 7, FIG. 17 is an end view of a tube when flattened in the regulator of the invention at the section line 11—11 of FIG. 7, FIG. 18 is an end view of a tube when flattened in the regulator of the invention at the section line 12—12 of FIG. 7, FIG. 19 is an end view of a tube when flattened in the regulator of the invention at the section line 13—13 of FIG. 7, FIG. 20 is a perspective of a second form of the invention, FIG. 21 is a side view showing a tube being engaged with the regulator of FIG. 20, FIG. 22 is a side view of a tube being operatively entered into the regulator of FIG. 20, FIG. 23 is an end view of a tube when partially regulated in a first modified form of the regulator of FIG. 5, FIG. 24 is an end view of a tube when closed to a maximum extent in the first modified form of the regulator of FIG. 5, FIG. 25 is an end view of a tube when partially regulated in a second modified form of the regulator of FIG. 5, and FIG. 26 is an end view of a tube when closed to a maximum extent in the second modified form of the regulator of FIG. 5.

FIG. 1 is a sectional elevation through a known apparatus. There is provided a channel body part 1 with part of the channel floor 2 cut away at 3. There are slots 4 in the channel walls angled to the plane of the channel floor 2. There is a roller 5 with stub axles 6 engaged in the slots 4. A tube 7 lying on the channel floor 2 is progressively squeezed by the periphery of the roller 5 as it is moved from the inoperative position shown in broken lines to the full operative position shown in full lines where the bore of the tube 7 is completely flattened thereby preventing flow of liquid through the bore of the tube 7. FIGS. 2 to 4 show several stages of a tube of circular cross-section, made for example from plastic, being squeezed between two flat surfaces such as the floor 2 of the channel 1 and the periphery of a roller, as provided in the apparatus of FIG. 1. The circular tube is flattened gradually until the configuration of FIG. 4 is achieved where the opposed inner surfaces of the tube bore come into contact and any flow of liquid through the tube bore is pinched stopped.

In the apparatus of the invention as illustrated in FIGS. 5 to 13 there is a channel member 8 with walls 9 and a bottom 10 which extends part way along the channel. There is an outwardy extending shoulder 11 on each channel wall 9 and there is an internal track 12 in each wall 9 extending into the respective shoulders 11. It will be noted that the tracks 12 are substantially parallel to the channel floor 10.

There is a roller 13 mounted in the channel with a thickness substantially the same as the width between the walls 9 and two stub-axles 14 extending from the respective sides of the roller 13 are engaged in the tracks 12.

Referring to FIGS. 6,7,9 to 12 it will be seen that there is a groove 15 in the floor 10 of the channel. The groove has a uniform depth and varying width. The groove at its wide end narrows quickly to a position indicated 16 and narrows at a slower rate to the end 17. FIGS. 9 to 13 indicated the cross-sectional shape of the groove 15 at the section lines 9 to 13. It will be noted in FIG. 13 that the gap between the the floor 10 of the channel and the periphery of the roller 13 is no greater than double the thickness of the wall of the tube 18. At the point of section line 13 the tube 18 will be closed off and liquid flow will be prevented. The shape of the tube at the section lines 9 to 13 are represented by the sectional shapes of the tube 18 shown in FIGS. 15 to 19. It will be noted that there is a natural tendancy for the portion of the tube 18 in the groove 15 to adopt a generally circular shape thereby ensuring that there is a minimum surface area for the cross-sectional shape of the liquid flow path.

FIG. 20 shows a modified form of the apparatus illustrated in FIG. 5. It will be observed that with the apparatus of FIG. 5 it is necessary to thread an end of the tube 18 through the channel between the roller 13 and the channel floor 9 and the tube end can then be attached to some other apparatus, for example a needle. This form of tube engagement can lead to contamination of the end of the tube and sterility is very important with medical equipment. The FIG. 20 apparatus allows the apparatus to be mounted on a tube whilst its ends are connected in a sterile manner to, say, a bottle of liquid and a needle thereby avoiding a possible source of contamination of the tube end to be coupled to the needle or the bottle.

Specifically, the apparatus of FIG. 20 is the same as that of FIG. 5 except that there is a slot 19 in one wall 9 of the channel. The slot 19 is adjacent the end 20 of the channel floor 10 and spaced from the roller 13. Referring now to FIG. 21, which is a side view of the FIG. 20 apparatus in the first stage of mounting a tube 18 therein. It will be seen that the tube 18 is passed through the slot 19 to the center of the channel and, as shown in FIG. 22, the channel member is rotated in an anti-clockwise direction to position the tube 18 below the roller 13 and in the channel in an overlying relationship with the channel floor 10. The roller 13 can then be advanced to co-act with the tube 18 as explained above.

FIGS. 23 to 26 illustrated two possible tube shaping where a predetermined minimum flow rate of liquid is desired. For example in FIG. 23 there is a continuous circumferential groove in the roller 13 and a groove 15 as explained above. In an intermediate position along the groove 15 the section of the tube would be as shown in FIG. 23, at say the position of the section line 11 of FIG. 7. FIG. 24 illustrated the cross-section of the tube 18 at the section line 13 of FIG. 7 where it will be seen that the bottom of the tube 18 is flat but there is a semi-circular shape to the top of the tube 18 ensuring a predetermined minimum flow of liquid through the tube 18.

FIGS. 25 and 26 are views of an arrangement similar to that of FIGS. 23 and 24 except that the groove 15 is central and not to one side of the channel floor 10. It will be understood that the groove 15 as described with reference to FIGS. 6,7,9 to 12 is preferably to one side of the channel floor but the groove 15 when used in conjunction with a flat surface roller 13 can be centrally located in the channel floor 10 as proposed for the FIG. 25 and 26 arrangement.

While the groove 15 has been described herein as being of uniform depth but varying width it is to be understood that this is not necessarily the case and both the depth and width of the groove 15 can be varied. With both arrangements as proposed the main objectives of the invention can be achieved, namely to keep the surface area of the cross-section of the bore tube 15 to a minimum for all sizes of bore and to try to maintain the bore substantially circular in cross-section for the smaller bore sizes.

I claim:

1. A Flow regulator for liquids passing through a resiliently deformable tube comprising
   an elongated body of channel shape having a bottom wall and two side walls, said side walls having a portion which extends beyond a first end of said bottom wall, a groove in the inner face of said bottom wall, said groove decreasing in cross sectional size as it extends from said first end of said bottom wall, a track in the inner face of each of said side walls, said tracks being parallel to each other and extending beyond said first end of the bottom wall, a wheel having a stub axle extending from each side adapted to be received in said tracks, the diameter of said wheel being such that as said wheel stub axles are moved along said tracks the periphery of said wheel will force a tube located in the regulator into said groove in the bottom wall, and a slot in one of said side walls extending transverse to the length of said side wall and completely through said side wall, said slot being located adjacent said first end of the bottom wall whereby the tube can be laid into the channel formed by the bottom wall and the side walls.

2. A regulator as claimed in claim 1 wherein the groove has a uniform depth and varying width along its length.

3. A regulator as claimed in claim 1 wherein one edge of said groove is adjacent to and parallel with one of said side walls.

4. A regulator as claimed in claim 1 wherein said tracks are parallel to the inner face of said bottom wall.

* * * * *